(12) United States Patent
Tasoglu et al.

(10) Patent No.: US 12,397,288 B2
(45) Date of Patent: Aug. 26, 2025

(54) FLUID ANALYSIS DEVICES

(71) Applicant: University of Connecticut, Farmington, CT (US)

(72) Inventors: Savas Tasoglu, Istanbul (TR); Reza Amin, Farmington, CT (US); Stephanie Knowlton, Walpole, MA (US)

(73) Assignee: University of Connecticut, Farmington, CT (US)

( * ) Notice: Subject to any disclaimer, the term of this patent is extended or adjusted under 35 U.S.C. 154(b) by 543 days.

(21) Appl. No.: 16/882,003

(22) Filed: May 22, 2020

(65) Prior Publication Data

US 2020/0368745 A1  Nov. 26, 2020

Related U.S. Application Data

(60) Provisional application No. 62/852,810, filed on May 24, 2019.

(51) Int. Cl.
*B01L 3/00* (2006.01)

(52) U.S. Cl.
CPC ... *B01L 3/502715* (2013.01); *B01L 3/502723* (2013.01); *B01L 2300/048* (2013.01); *B01L 2300/161* (2013.01); *B01L 2300/168* (2013.01)

(58) Field of Classification Search
None
See application file for complete search history.

(56) References Cited

U.S. PATENT DOCUMENTS

| | | | |
|---|---|---|---|
| 9,687,845 B2 | 6/2017 | Weibel et al. | |
| 2002/0125139 A1 | 9/2002 | Chow et al. | |
| 2007/0240773 A1* | 10/2007 | Zimmermann | F16K 99/0001 137/557 |
| 2011/0059547 A1* | 3/2011 | Dehal | G01N 33/54326 422/68.1 |
| 2011/0123398 A1* | 5/2011 | Carrilho | F16K 99/0001 422/68.1 |
| 2012/0040470 A1 | 2/2012 | Dorn et al. | |
| 2013/0280698 A1* | 10/2013 | Propper | B01L 3/5027 422/402 |

(Continued)

FOREIGN PATENT DOCUMENTS

| | | |
|---|---|---|
| CA | 2468245 A1 | 6/2003 |
| CN | 101578520 A | 11/2009 |

(Continued)

OTHER PUBLICATIONS

Yu et al. "Emergering technologies for home-based semen analysis" Andrology 2018; pp. 10-19.

(Continued)

*Primary Examiner* — Matthew D Krcha
(74) *Attorney, Agent, or Firm* — Lisa Mueller; Casimir Jones SC

(57) ABSTRACT

A fluid analysis device can include a fluid inlet opening configured to receive a test fluid, and one or more fluid distribution channels in fluid communication with the fluid inlet opening and configured to receive and distribute the test fluid from the fluid inlet opening using a passive self-loading mechanism. The device can include a plurality of assays fluidly isolated from each other and configured to receive the test fluid from the one or more fluid distribution channels.

13 Claims, 6 Drawing Sheets

(56) References Cited

U.S. PATENT DOCUMENTS

| | | | |
|---|---|---|---|
| 2014/0199720 A1* | 7/2014 | Qiu | B01L 3/502746 600/35 |
| 2014/0358036 A1* | 12/2014 | Holmes | A61B 5/150343 600/575 |
| 2016/0289669 A1* | 10/2016 | Fan | B01L 3/502761 |
| 2018/0181792 A1 | 6/2018 | Shafiee | |
| 2018/0348207 A1 | 12/2018 | Nosrati et al. | |
| 2019/0168223 A1* | 6/2019 | Soto-Moreno | C12M 23/16 |

FOREIGN PATENT DOCUMENTS

| | | | |
|---|---|---|---|
| CN | 102387863 A | 3/2012 | |
| CN | 108088841 A | 5/2018 | |
| EP | 3113886 A1 | 1/2017 | |
| JP | 2002507480 A | 3/2002 | |
| JP | 2016538858 A | 12/2016 | |

OTHER PUBLICATIONS

Nosrati et al. "Paper Based Quantification of Male Fertility Potential" Clinical Chemistry 2016; 62:3; pp. 458-465.

Martinez, Andrew W., et al., "Diagnostics for the Developing World: Microfluidic Paper-Based Analytical Devices," Analytical Chemistry, 82(1):3-10 (2009).

* cited by examiner

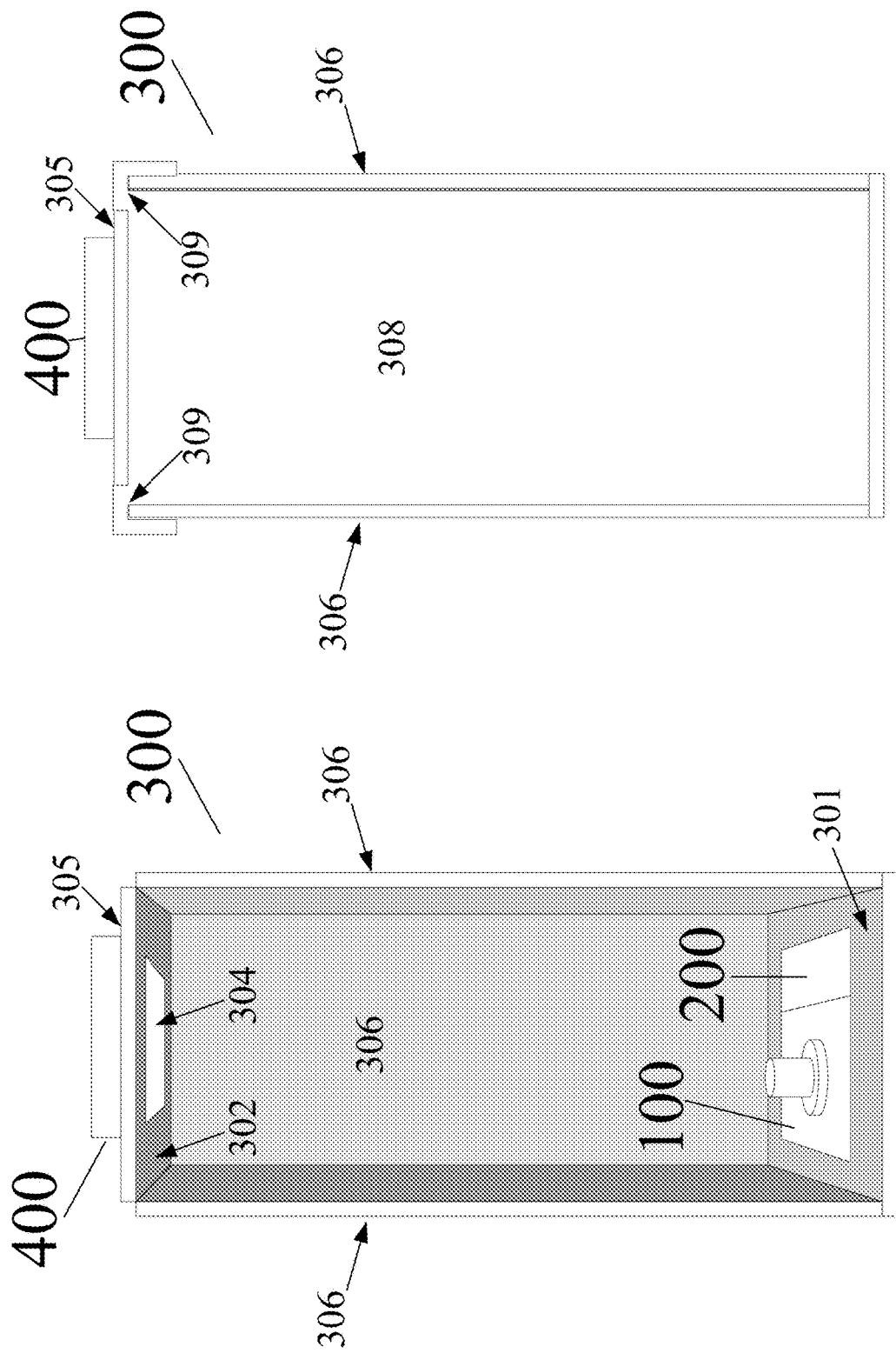

FLUID ANALYSIS DEVICES

CROSS-REFERENCE TO RELATED APPLICATIONS

This application claims priority to and the benefit of U.S. Provisional Application No. 62/852,810, filed May 24, 2019, the entire contents of which are herein incorporated by reference in their entirety.

FIELD

This disclosure relates to fluid analysis devices.

BACKGROUND

Certain fluid analysis devices are configured for sperm analysis. Traditional fluid assays, e.g., for analyzing sperm, do not include one or more desired tests, and/or are expensive and/or complicated.

Such conventional methods and systems have generally been considered satisfactory for their intended purpose. However, there is still a need in the art for improved methods, systems, and devices for analyzing fluids, e.g., bodily fluids, such as, for example, semen. The present disclosure provides a solution for this need.

SUMMARY

A fluid analysis device can include a fluid inlet opening configured to receive a test fluid, and one or more fluid distribution channels in fluid communication with the fluid inlet opening and configured to receive and distribute the test fluid from the fluid inlet opening using a passive self-loading mechanism. The device can include a plurality of assays fluidly isolated from each other and configured to receive the test fluid from the one or more fluid distribution channels.

In certain embodiments, the device can include an inlet layer defining the fluid inlet opening. In certain embodiments, the device can include one or more distribution layers attached to the inlet layer and forming the one or more fluid distribution channels. In certain embodiments, the device can include an assay layer having the plurality of assays disposed thereon. Any other suitable construction (e.g., a unitary construction for the device) is contemplated herein.

In certain embodiments, the device can include one or more vertical channel layers disposed between the one or more distribution layers and the assay layer and having a plurality of fluidly isolated vertical channels. The plurality of vertical channels can be configured to align a portion of the one or more fluid distribution channels with a respective assay on the assay layer.

The one or more fluid distribution channels can have a plurality of fluid paths that extend from a trunk portion, each fluid path terminating into one or more termini in fluid communication with a respective vertical channel. In certain embodiments, only the one or more termini can be in fluid communication with the vertical channels.

The plurality of fluid paths can reduce in flow area to cause substantially even distribution to each terminus. For example, each fluid path can include a branch in fluid communication with the trunk and having a branch flow area, a stalk in fluid communication with the branch and having a stalk flow area smaller than the branch flow area, and one or more stems in fluid communication with the stalk and having a stem flow area smaller than the stalk flow area.

Each fluid path can be fluidly isolated from the other fluid paths to prevent bubble trapping, for example.

In certain embodiments, the inlet layer can include a plurality of vent holes defined therein in fluid communication with the one or more fluid distribution channels to allow air flow through the plurality of vent holes (to prevent bubble trapping along with and/or separate from isolated fluid paths, for example). Any suitable number, position, pattern, and/or size of vent holes is contemplated herein.

The one or more distribution layers can include and/or are formed from a channel layer material that is configured to be wetted by the test fluid. For example, the channel layer material can be hydrophilic (e.g., for a water based fluid, e.g., semen).

In certain embodiments, the assay layer can be made of an assay layer material that is configured to be wetted by the test fluid. In certain embodiments, each assay can be surrounded by a non-wettable material to fluidly isolate each assay from each other and/or from the assay layer material.

In certain embodiments, the device can include a clear bottom layer (e.g., a glass layer or a transparent plastic layer, or any other suitable transparent or at least partially transparent layer) disposed on an underside of the assay layer. The clear bottom layer can be configured to allow viewing of each assay result and/or each assay.

In certain embodiments, the device can include a mask connected to the one or more vertical channel layers and configured to permanently or selectively reduce and/or filter a flow area of the one or more vertical channels (e.g., to provide a sperm motility test). Any suitable size, shape, and number of masks to cover any suitable portion of any suitable vertical channels are contemplated herein.

In certain embodiments, the device can include one or more adhesive layers configured to adhere and seal one or more other layers together. The one or more adhesive layers can include one or more complimentary channels and/or holes defined therein to allow flow therethrough, for example. In certain embodiments, the device can include an inlet reservoir in fluid communication with the inlet opening and configured to receive the test fluid from a user.

In accordance with at least one aspect of this disclosure, a fluid analysis device can be configured to receive a test fluid and to uniformly distribute the test fluid to a plurality of fluidly isolated assays. In certain embodiments, the test fluid can be semen.

In accordance with at least one aspect of this disclosure, a method can include analyzing a device as disclosed herein, e.g., as described above, in photographic analysis container using an imaging device and an image processor (e.g, a smartphone, tablet, etc.). The method can include any other suitable method and/or portions thereof.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIG. 6A is a cross-sectional view of an embodiment of open photographic analysis container in accordance with this disclosure; and FIG. 6B is a cross-sectional view of an embodiment of a photographic analysis container in accordance with this disclosure.

DETAILED DESCRIPTION

Figure 1:
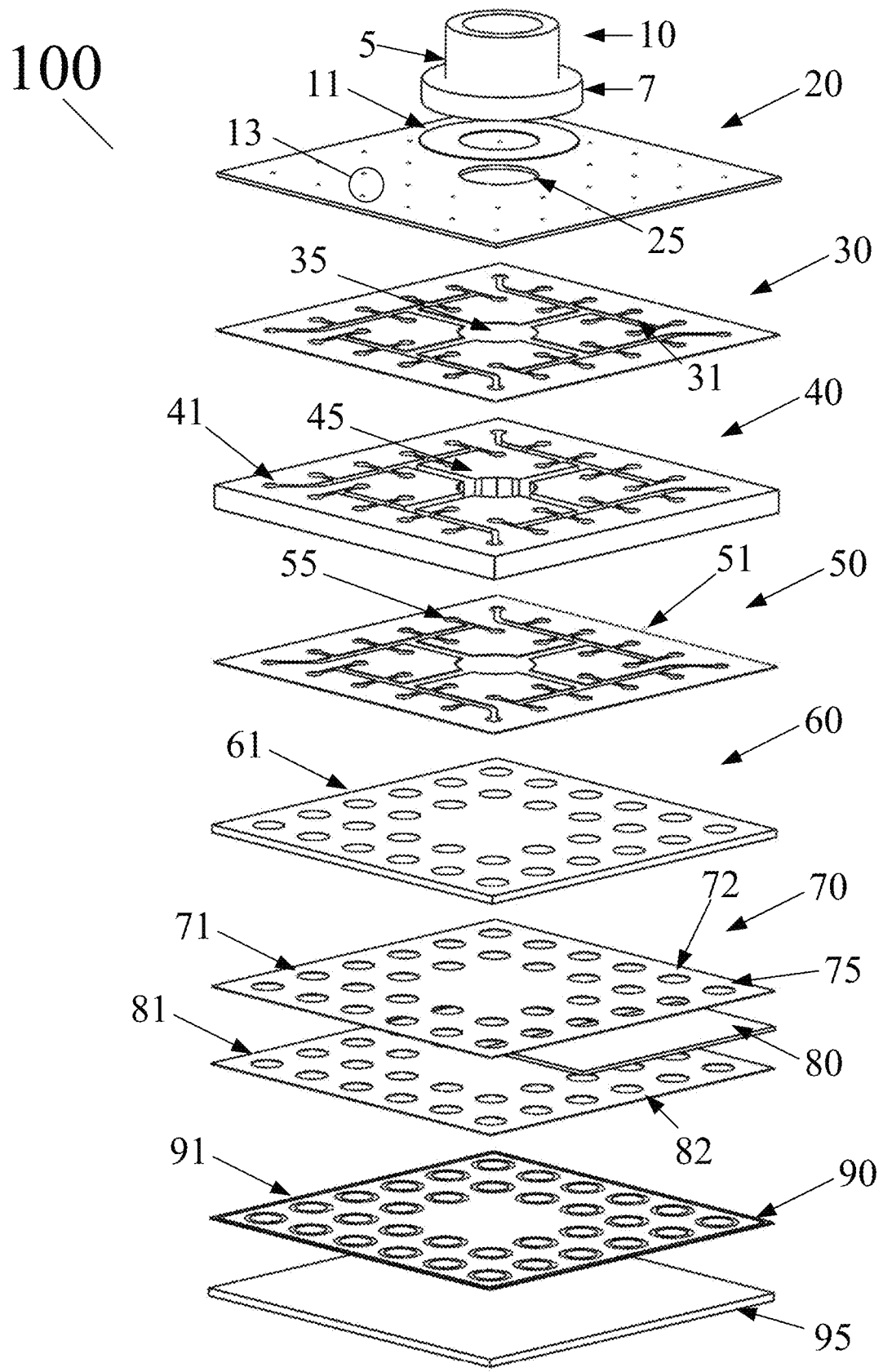
FIG. 1 shows an exploded isometric view of an embodiment of a device in accordance with this disclosure.

Reference will now be made to the drawings wherein like reference numerals identify similar structural features or aspects of the subject disclosure. For purposes of explanation and illustration, and not limitation, an illustrative view of an embodiment of a device in accordance with the disclosure is shown in FIG. 1 and is designated generally by reference character 100. Other embodiments and/or aspects of this disclosure are shown in FIGS. 2-6B. Embodiments disclosed herein can be used to analyze fluids, e.g., body fluids, e.g., semen. Any other suitable use (e.g., oil analysis, water analysis, or any other suitable fluid) is contemplated herein.

Referring to FIGS. 1-5B, a fluid analysis device (e.g., device 100) can include a fluid inlet opening (e.g., opening 25) configured to receive a test fluid (e.g., semen). The device 100 can include one or more fluid distribution channels (e.g., comprising portions 31, 41, 51, 35, 45, 55) in fluid communication with the fluid inlet opening and configured to receive and distribute the test fluid from the fluid inlet opening (e.g., opening 25) using a passive self-loading mechanism. The passive self-loading mechanism can include one or more of static pressure from the fluid inlet opening that can be above fluid distribution channels (e.g., head pressure produced by a filled reservoir 10) and/or capillary action (e.g., which can be generated based on one or more of the size and/or shape of the fluid distribution channels, and/or the material the fluid distribution channels are made from, and/or the fluid characteristics of the fluid that is being tested such as viscosity for example). Any other suitable mechanism is contemplated herein. The device can include a plurality of assays (e.g., assay areas 91) fluidly isolated from each other and configured to receive the test fluid from the one or more fluid distribution channels.

In certain embodiments, the device can include an inlet layer (e.g., layer 20) defining the fluid inlet opening (e.g., opening 25). The inlet layer can be made of any suitable material, e.g., material that is non-wettable by the test fluid (e.g., hydrophobic material). Any suitable mouth or inlet portion can be attached to or formed from the inlet layer (e.g., reservoir 10) to direct a test fluid into the fluid inlet opening.

In certain embodiments, the device can include one or more distribution layers (e.g., one or more of layers 30, 40, and 50) attached to the inlet layer and forming the one or more fluid distribution channels. Any suitable number of layers, e.g., one, two, three as shown, are contemplated herein. The entirety of the one or more fluid distribution channels can be defined through the entire thickness of the layer, for example, e.g., as shown. In certain embodiments, only a portion may be open to a top (e.g., an inlet end) and a portion may be open to a bottom (e.g., an outlet end). Any other suitable channels are contemplated herein (e.g., only a portion being defined through the entire thickness).

The one or more fluid distribution channels can be microfluidic channels (e.g., to allow flow via the capillary effect), for example. Any suitable size channels for any suitable use is contemplated herein.

In certain embodiments, the device can include an assay layer (e.g., layer 90) having the plurality of assays (e.g., one or more chemical or biological test areas) disposed thereon. Any suitable type of assay is contemplated herein.

While an embodiment is shown having a plurality of layers, any other suitable construction (e.g., a unitary construction for the device) is contemplated herein.

In certain embodiments, the device can include one or more vertical channel layers (e.g., one or more of layers 60, 70, 80) disposed between the one or more distribution layers and the assay layer. The one or more vertical layers can include having a plurality of fluidly isolated vertical channels (e.g., holes 71, 72, 81, 82). The plurality of vertical channels can be configured to align a portion (e.g., termini 4, 7) of the one or more fluid distribution channels with a respective assay on the assay layer. Any suitable number of vertical channel layers, e.g., one, two, three as shown, are contemplated herein.

As shown, for example, the one or more fluid distribution channels can have a plurality of fluid paths that extend from a trunk portion 35, 45, 55, each fluid path terminating into one or more termini 4, 7 in fluid communication with a respective vertical channel. In certain embodiments, only the one or more termini 4, 7 can be in fluid communication with the vertical channels. In this regard, in certain embodiments, the rest of the fluid distribution channels can be blocked on a bottom side thereof by the vertical channel layer or other suitable blocking material or layer, for example.

As shown, the plurality of fluid paths can reduce in flow area to cause substantially even distribution to each terminus 4, 7. For example, each fluid path can include a branch 1a, 1b, 1c, 1d in fluid communication with the trunk 35, 45, 55 and having a branch flow area, a stalk in fluid communication with the branch and having a stalk flow area smaller than the branch flow area, and one or more stems in fluid communication with the stalk and having a stem flow area smaller than the stalk flow area. Each fluid path can be fluidly isolated from the other fluid paths to prevent bubble trapping (e.g., in conjunction with one or more vent holes disclosed herein), for example, e.g., as shown.

In certain embodiments, the inlet layer can include a plurality of vent holes (e.g., 13) defined therein in fluid communication with the one or more fluid distribution channels (e.g., placed over each termini 4, 7) to allow air flow through the plurality of vent holes (e.g, to facilitate flow of the test fluid through the one or more fluid distribution channels and/or to prevent bubble trapping along with and/or separate from isolated fluid paths, for example). Any suitable number, position, pattern, and/or size of vent holes is contemplated herein.

The one or more distribution layers (e.g., layer 40) can include and/or can be formed from a channel layer material that is configured to be wetted by the test fluid, for example. For example, the channel layer material can be hydrophilic (e.g., for a water based fluid, e.g., semen). For example, the channel layer material, e.g., for layer 40 can be Polymethyl methacrylate or any other suitable material. In certain embodiments, layers 30 and 50 may be or represent adhesive layers (e.g., formed from or made of any suitable adhesive material) for bonding layer 40 to other layers. Any other suitable material and/or combinations thereof is contemplated herein.

The one or more vertical channel layers (e.g., layer 60) can be made of the same material as or different material from the channel layer material. Any suitable material is contemplated herein.

In certain embodiments, the assay layer can be made of an assay layer material that is configured to be wetted by the test fluid (e.g., paper). In certain embodiments, as shown in FIG. 1) each assay can be surrounded by a non-wettable material (e.g., a polymer) to fluidly isolate each assay from each other and/or from the assay layer material.

Figure 2:
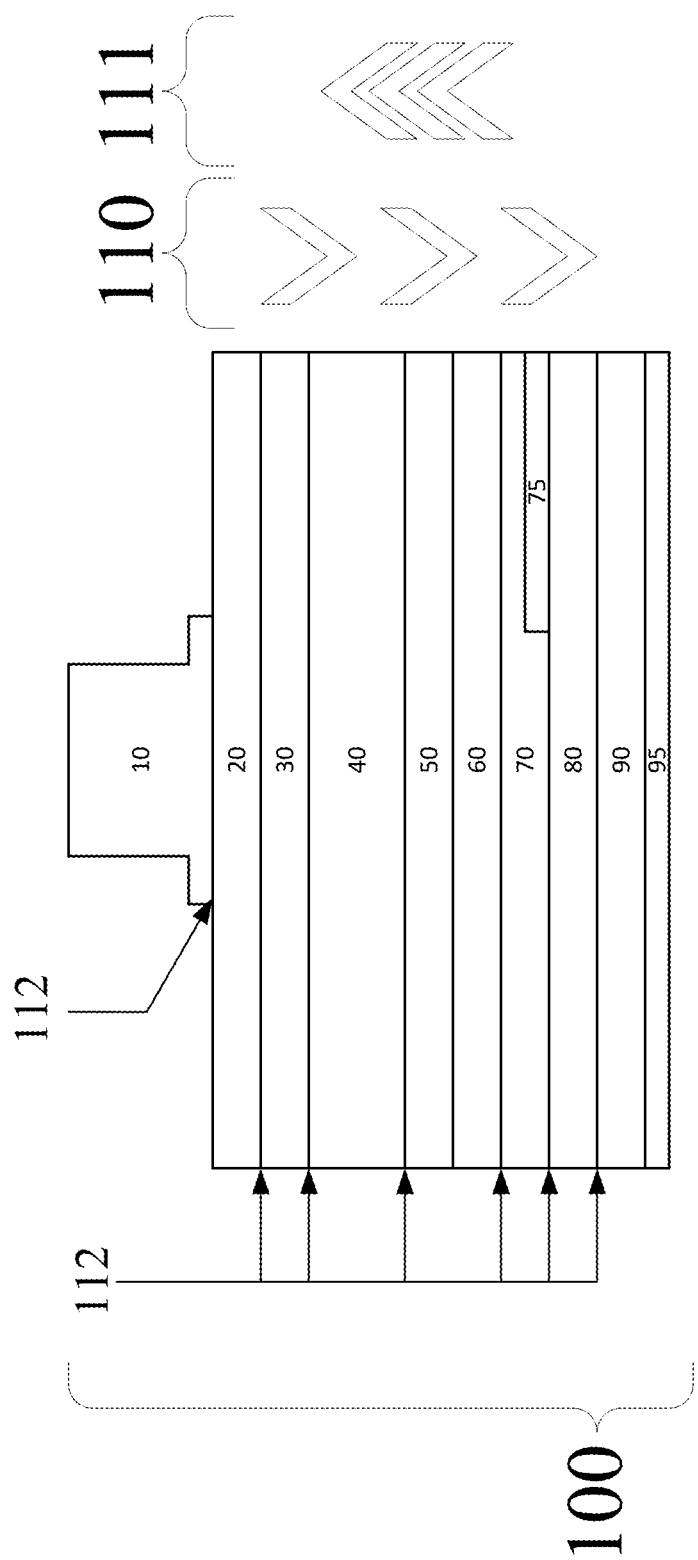
FIG. 2 is an elevation view of the embodiment of FIG. 1.

In certain embodiments, the device can include a clear bottom layer (e.g., a glass layer or a transparent plastic layer, or any other suitable transparent or at least partially transparent layer), e.g., layer 95, disposed on an underside of the assay layer. The clear bottom layer can be configured to allow viewing of each assay result and/or each assay (e.g., when assembled as shown in FIG. 2). It is contemplated that the assay layer may be a clear layer with the assays directly disposed thereon (e.g., indicator deposited on the function surface thereof) and/or fluidly isolated from each other.

In certain embodiments, the device can include a mask (e.g., membrane 75) connected to the one or more vertical channel layers and configured to permanently or selectively reduce and/or filter a flow area of the one or more vertical channels (e.g., to provide a sperm motility test). For example, the mask can be a membrane 75 that is configured to filter one or more particles. In certain embodiments, the membrane 75 can be configured to be a physical separation having small holes (e.g., 5 micrometers) and/or tortuous fluid pathways such that only live sperm are capable of swimming through. In certain embodiments, the mask can be a chemical filter that chemically reacts with and filters out certain compounds. In certain embodiments, the mask can be any suitable selectively permeable membrane. Any suitable type of mask and/or membrane are contemplated herein. Any suitable size, shape, and number of masks to cover any suitable portion (e.g., all of, part of) of any suitable vertical channels are contemplated herein. In certain embodiments, the layers 70 and/or 80 may be one or more adhesive layers and/or have a mask (e.g., membrane 75) disposed therebetween to partially block and/or filter one or more of the vertical channels (e.g., as shown in FIG. 1).

In certain embodiments, e.g., as partly described above, the device can include one or more adhesive layers (e.g., layers 30, 50, 70, 80) configured to adhere and seal one or more other layers together. The one or more adhesive layers can include one or more complimentary channels and/or holes defined therein to allow flow therethrough, for example. In certain embodiments, the device can include an inlet reservoir 10 in fluid communication with the inlet opening and configured to receive the test fluid from a user. It is contemplated that one or more of these adhesive layers need not be used and certain, if not all layers, can be bonded together in any other suitable manner.

In accordance with at least one embodiment of this disclosure, referring to FIGS. 1 and 2, a fluid analysis device 100 can include a reservoir 10 having a well 5 and a flange 7 for receipt of a sample for analysis, e.g., a semen sample. The device 100 may also have a gasket 11 (e.g., a compression seal), e.g., lined with double-sided adhesive ("DSA") 112 such as types known to those skilled in the art, which may be used to attach reservoir 10 to a vented hydrophilic layer 20. Any suitable seal and/or attachment means is contemplated herein. For example, certain embodiments can include double sided tape or other suitable adhesive, without a gasket, which can act as gasket. For example, certain embodiments can be thermal fusion sealed, glued, or any other suitable sealing joint between components (e.g., a braze joint between the layers), and embodiments with no separate sealing layer or adhering layer are contemplated herein.

A vented hydrophilic layer 20 may comprise a fluid inlet opening 25 and a plurality of vent holes 13 through the thickness of the hydrophilic layer 20. In certain embodiments, vent holes 13 may be about 100 microns. The holes 13 (and/or any other suitable hole and/or aperture, channel, etc.) can be formed via any suitable method of manufacturing (e.g., laser cutting, stamping, molding, additive manufacturing, die cutting, milling, or other machining or and/or suitable processes known to those skilled in the art).

The device 100 may also comprise an upper channel layer 30 containing an upper trunk 35 surrounded by a microfluidic branched system 31, an intermediate channel layer 40 having an intermediate trunk 45 surrounded by a microfluidic branched system 41, and a lower channel layer 50 having a lower trunk 55 surrounded by a microfluidic branched system 51. In certain embodiments one or more of upper channel layer 30, intermediate channel layer 40, and lower channel layer 50 may be lined on one more sides with a DSA 112 in order to adhere to other layers comprising device 100. Other methods of assembly of device 100 and its constituent layers may include binding the layers using thermoset lamination, using roll-to-roll fabrication to cut, align, and laminate/bind layers, and other techniques known to those skilled in the art.

In certain embodiments, the device 100 may also comprise a hydrophilic layer 60 attached below the lower channel layer 50 to close lower trunk 55 while providing a plurality of flow-through holes 61 that selectively overlap microfluidic branched system 51. In certain embodiments, hydrophilic layer 60 may be adhered to another layer comprising device 100 using DSA 112.

The device 100 may also include a membrane 75 for selective detection schemes for analysis of fluids placed into device 100. In certain embodiments, a membrane 75 may be located between an upper hydrophilic polycarbonate layer 70 having a plurality of through-holes 71 and a lower polymer film layer 80, which may be a hydrophilic polycarbonate or DSA, having a plurality of through-holes 81. In certain, membrane 75 may impede flow of fluid from a restrictive through-hole 72 to its corresponding restrictive through-hole 82 or through-holes in lower layer 80 adjacent thereto.

In certain embodiments, the device 100 may comprise a detection layer 90 which may be a paper-based assay (e.g., a colorimetric assay) having a plurality of hydrophobic barriers 92 with each barrier 92 enclosing its respective assay area 91. The device 100 may further comprise a polymer lamination layer 95 affixed to the bottom of device 100. A means of affixing each of the foregoing layers to one another to form device 100 may be DSA 112.

In certain embodiments, various through-going openings in the layers may be substantially aligned or offset by predetermined distances depending on the analysis conducted and/or needs of the testing. For example, in certain embodiments, the opening in reservoir 10 may be substantially aligned with one or more of trunk portions 25, 35, 45, and 55. In certain embodiments, the microfluidic branched system 31 may be substantially aligned with one or more of microfluidic branched system 41 and microfluidic branched system 51. In a further embodiment, at least one of flow-through holes 61 may be substantially aligned with at least one flow-through hole 71, flow-through hole 81, and/or assay area 91.

In certain embodiments, reservoir 10 may be 3D printed, molded, or otherwise made out of any suitable hydrophobic material known to those skilled in the art. While reservoir 10 may have a conical shape and rectangular cross-section, a nozzle-like reservoir 10 may be utilized having a larger entry and a narrower exit in contact with fluid inlet opening 25 of a hydrophilic layer 20 in a rectangular or conical shape and trapezoidal cross-section. In certain embodiments, reservoir 10 may be sized so as to maintain the hydrostatic pressure to allow flow of sample having viscosity between about 1 cP and about 10 cP to disperse throughout the microfluidic branched systems 31/41/51 within about 6 seconds. In certain embodiments, reservoir 10 may be about 1 cm in height and have a radius between about 2.5 mm to about 7.5 mm or any such radius sized to ensure enough sample volume to be analyzed in the device 100.

In certain embodiments, a reservoir 10 may be additively manufactured (e.g., 3D printed with clear resin) and affixed to the top of the layered device 100 (e.g., as described above) using a piece of double-sided adhesive (DSA) cut into an annulus, for example (e.g., using a laser cutter). Such a reservoir 10 may hold a volume of about 1 mL of a sample of body fluid, for example, a semen sample for fertility or other forms of testing. Any other suitable amount is contemplated herein.

In certain embodiments, hydrophilic layer 20 may be transparent and fabricated from a polymer film. A vent 13 in hydrophilic layer 20 may be used to release air while a sample is introduced into reservoir 10. In certain embodiments, air flow 111 out of device 100 may be had via one or more of vents 13 as the flow of sample 110 descends through device 100 (as illustratively provided for in FIG. 2). Accordingly, as a sample flows into each of the microfluidic channels, air previously residing in those spaces is displaced out of device 100 via the vents 13. Consequently, in certain embodiments, vents 13 in a hydrophilic layer 20 may relieve pressure in device 100 so that more sample may permeate into device 100 and throughout a given portion or all of a microfluidic channel. In certain embodiments, there may be one vent 13 for each assay area 91.

In certain embodiments, channel layers 30, 40, and 50 may be made from a hydrophilic polymer film, e.g. PCA acrylic. The layers 30, 40, 50 can be formed (e.g., laser cut), e.g., with or without the DSA 112 applied, to have a pattern to serve as a microfluidic channel, such as the channels in microfluidic branched system 31, 41, and 51 for example. Where a channel layer 30/40/50 is comprised of a hydrophilic material, one advantage is facilitation of flow of a sample from reservoir 10 throughout the microfluidic branched system 31, 41, and 51. One advantage to such microfluidic branched system 31, 41, and/or 51 may be to provide a polymer film layer, such as a polycarbonate, as a continuous piece, rather than having isolated cut regions that may fall out during assembly.

In certain embodiments, hydrophilic layer 60 attached below the lower channel layer 50 may provide through-going passage for sample to flow from the microfluidic branched system 51 towards the paper-based assay layer 90. In certain embodiments, layer 60 may be laser cut using a laser cutter, like layers 20-50 and 70. In certain embodiments, the laser cut layers of device 100 may be between about 0.01" and about 0.03" in thickness and made from a polymer film, such as, for example, a polycarbonate. In certain embodiments, polycarbonate layers of thickness of 0.01", 0.02", and 0.03." In certain embodiments of layers 30-50, such layers may be made of a polycarbonate the polycarbonate and DSA 112 are received with protective layers on both sides and left in place during cutting and removed immediately before device 100 assembly.

In certain embodiments, a paper-based assay layer 90 may be designed to have numerous regions 91 designed to measure different parameters of interest for a given sample. In certain embodiments, assay 90 regions may have regions that test for sperm concentration, sperm motility, semen pH, and semen fructose level, all in the case of fertility testing. In certain embodiments, a desired reagent is pipetted into the assay region 91 on the layer 90 within a plotted hydrophobic barrier 92 (see FIG. 5A) prior to device 100 assembly. A typical drying time for such an assay reagent was 24 hours at room temperature prior to device assembly. In certain embodiments, assay layer 90 may comprise 32 assay regions 91 surrounded by hydrophobic barriers 92 having approximately 5 mm diameters.

As described herein, a laser cutting utility for assay layer 90 may comprise a hybrid cutter-plotter comprised an XY motorize axis with both a pen plotter known to those skilled in the art. Any other suitable patterning technique is contemplated herein, e.g., digital printing, screen printing, and stamping. A plotter may pattern the hydrophobic barriers 92 of assay layer 90 using a plotter controlled by eleksCAM software with a pre-determined offset, for example, an offset of approximately 1 mm in x-axis and approximately 33 mm in y-axis. Such a pre-determined offset may be based on the spatial offset between the plotting pen and the laser such that the plotted hydrophobic barriers 92 and laser-cut microfluidic branched system 31/41/51 and/or through-holes 61/71/72/81/82 would be substantially aligned.

Any other suitable cutter is contemplated herein. Any suitable method of cutting and/or otherwise forming channels are contemplated herein.

Figure 3:
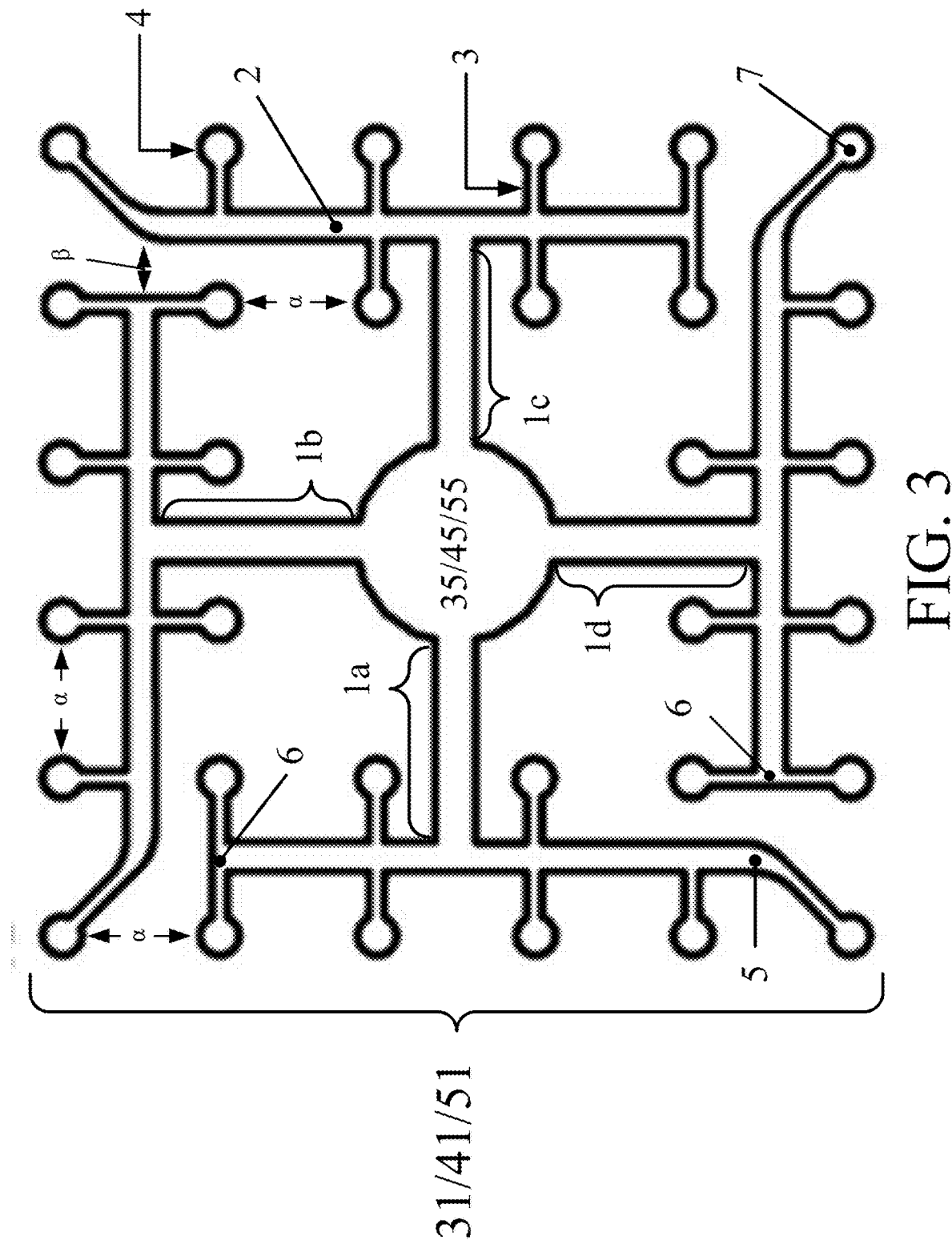
FIG. 3 is a top plan view of a portion of the embodiment of FIG. 1, showing an embodiment of microfluidic channels.
Figure 4C:
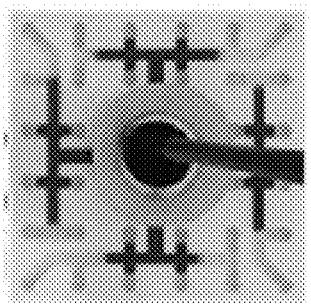
FIGS. 4A, 4B, 4C, 4D, 4E, and 4F illustrate fluid dissemination over time for a fluid within the embodiment of microfluidic channels of FIG. 3.
Figure 4F:
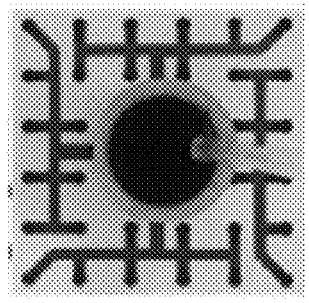
Figure 4B:
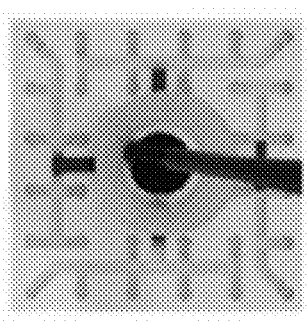
Figure 4E:
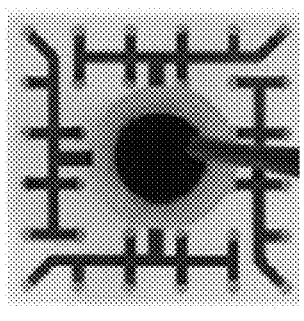
Figure 4A:
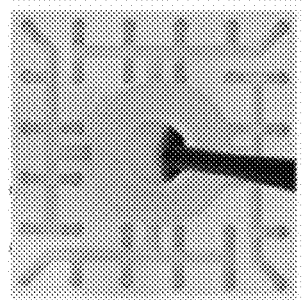
Figure 4D:
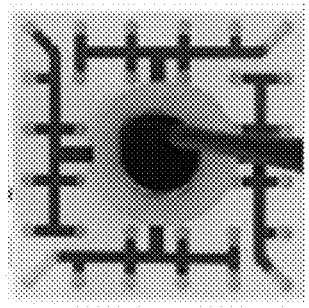

With reference to the illustrative embodiments of a microfluidic branched system 31/41/51 of FIGS. 3 and 4A, a fluid sample may be deposited in a reservoir 10 and flow into one or more of trunk sections 34/45/55. With further reference to FIGS. 3 and 4B, the fluid sample may then flow outwardly from a trunk section 34/45/55 along branches 1a, 1b, 1c, and/or 1d. With further reference to FIGS. 3 and 4C, the fluid sample may then projects into a stalk 2 extending away from a respective branch 1a-d. In certain embodiments, as shown in FIG. 4C, the fluid sample may disseminate into one or more stems 3 located most proximal to the stalk 2 and branch 1a-d junction, terminating in at least one terminus 4 attached to a respective stem 3. Referring to FIGS. 3 and 4D, the fluid sample may disseminate into substantially all of stems 3 and their corresponding termini 4, although in certain cases, the design of the microfluidic branched system 31/41/51 may only allow fluid to reach all stumps 6 of a particular stalk 2, but not the elbow 5 and its respective angled terminus 7 for the particular stalk 2. However, as FIGS. 4E and 4F may illustrate, the fluid sample over time may substantially fill all sectors of the microfluidic branched system 31/41/51. While the thicknesses of the branch 1a-d, stalk 2, stem 3 and/or elbow 5 of a microfluidic branched system may differ, it may also be contemplated that these sections are substantially the same thickness. It should be understood that the flow of fluid through any one microfluidic branched system takes place in three dimensions (e.g., in the plane of the microfluidic branched system 31/41/51 and along the thickness of device 100 between layers 30, 40, and/or 50).

In certain embodiments, a sample of fluid may travel through a group of microfluidic branched system 31/41/51 of a device sized 7 cm by 7 cm in cross-section (when viewed from above) as shown and described with reference to FIGS. 3 and 4A-F as follows:

| Fluid Viscosity (cP) | Microfluidic channel thickness (branch/stalk/stem) (μm) | Fluid Delivery Time To All Termini (seconds) |
|---|---|---|
| 2 | 250 | 1.8-4.1 |
| 4 | 500 | 0.6-1.9 |
| 6 | 750 | 0.5-2.1 |

Figure 5B:
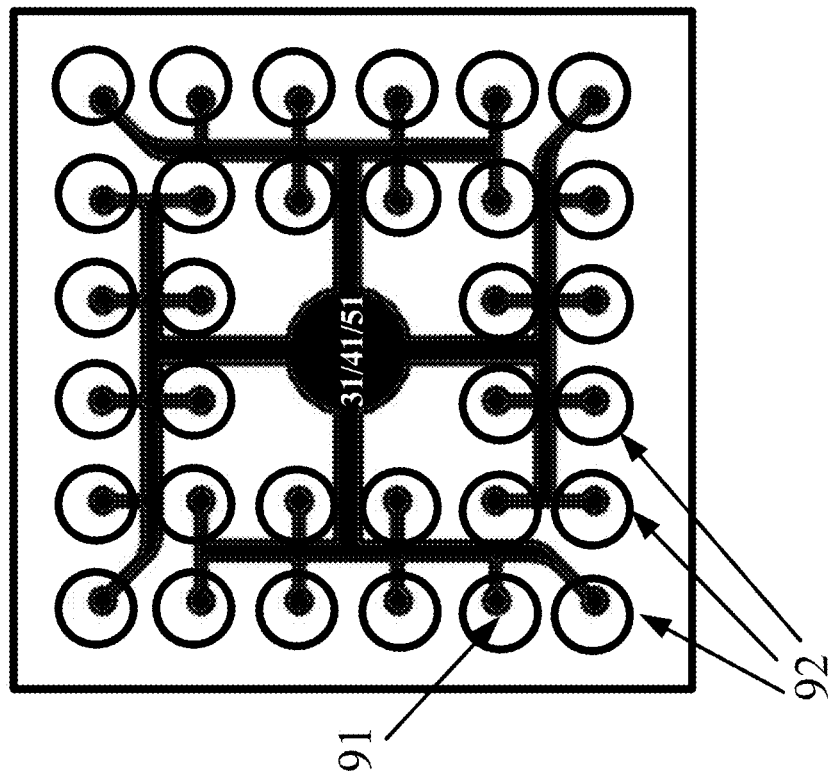
FIG. 5B is a top plan view of embodiments of portions of at least two layers of the device of FIG. 1.
Figure 5A:
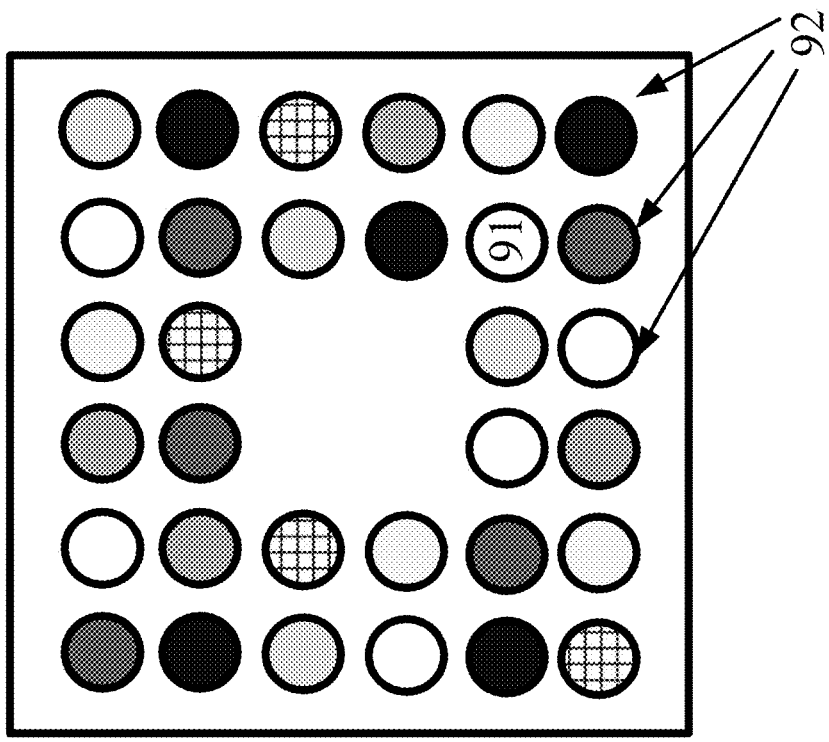
FIG. 5A is a top plan view of an embodiment of an assay portion of the device of FIG. 1.

Referring to the illustrative embodiment of FIG. 5A, an assay layer 90 may be illustrated with a plurality of different assay spots 91 surrounded by hydrophobic barriers 92. In certain embodiments, where the assay spots 91 are designed to measure sperm concentration, semen pH, and semen fructose level, these assay spots 91 or detection zones may be designed as follows. For assay spots 91 meant to detect sperm concentration, in certain embodiments, 2 μL of 5 mg/mL MTT (3-(4,5-dimethyl-2-thiazolyl)-2,5-diphenyl-tetrazolium bromide) may be dissolved in distilled water and deposited in each detection zone 91 and left to dry at room temperature. In certain embodiments, the yellow tetrazolium dye may be converted to purple formazan by the diaphorase flavoprotein enzyme existing in metabolically active sperm thereby causing a color change that may be interpreted as a measure of sperm concentration. In certain embodiments, a calibration of the sperm count assay may involve taking 5 μL of liquefied semen samples (sperm counts ranging from of 0 to 50 million/mL) and apply the same to each detection zone 91 and thereafter measure the color change after approximately 15 minutes.

In certain embodiments, for assay spots 91 meant to detect semen pH, three pH indicators (bromocresol green, bromothymol blue, and thymol blue) may be dissolved at concentrations of 0.8, 0.8, and 0.4 mg/mL, respectively, in deionized (DI) water with 0.9 mM sodium hydroxide (NaOH), 0.9 mM NaOH, and 0.8 mM NaOH, respectively, to aid in dissolution. Following this preparation, 2 μL of each reagent solution may be deposited in each detection zone 91 and left to dry at room temperature. In certain embodiments, the color change of each reagent in each pH detection zone 91 may be calibrated by individually applying 5 μL of different pH buffers ranging from 4 to 10 with 1 mg/mL chymotrypsin (as used for liquefaction of semen samples) and thereafter measuring the color change after approximately 15 minutes.

In certain embodiments, for assay spots 91 meant to detect semen fructose, a fructose assay may be based on a colorimetric glucose assay known to those skilled in the art, such as, for example, the Glucose (GO) Assay Kit from Sigma Aldrich located in St. Louis, Missouri, and preceded by a conversion of fructose to glucose. In certain embodiments, in a first step, fructose may be converted to glucose using a glucose isomerase enzyme. In certain embodiments, in a second step, using reagents known to those skilled in the art, such as Glucose oxidase/peroxidase reagent from Sigma Aldrich of St. Louis, Missours, the glucose may be oxidized by a glucose oxidase enzyme to produce hydrogen peroxide, which then may serve as a reactant in the enzymatic conversion of the iodide in KI brown-colored iodine by a peroxidase. An assay meant to detect semen fructose may be calibrated with different concentrations of fructose solutions ranging from 0 to 4 mg/mL and thereafter measuring the color change after approximately 15 minutes.

Referring to the illustrative embodiment of FIGS. 3 and 5B, a microfluidic branched system 31/41/51 may be aligned with through-holes 61/71/81 and/or assay zones 91 such that a substantial amount of the fluid sample from reservoir 10 reaches each of the assay zones 91 to increase resolution of results obtained for the particular fluid sample. For example, the distance a between termini 4 and/or 7 may be substantially the same as a distance between adjacent assay zones 91 and/or through-holes 61/71/81. In certain embodiments, assay zones 91 may be aligned with one or more termini 4/7 of a microfluidic branched system 31/41/51 to maximize consistent delivery of fluid samples to the assay zones 91. It has been found that maximized delivery of fluid samples has been achieved using orthogonal microfluidic channel arrangements of branches/stalks/stems rotated about their corresponding trunks through which fluid samples flow. Thus, while the illustrative arrangement of microfluidic branches 1a-d, stalks 2, stems 3, elbows 5, stumps 6, and elbow termini 7 may provide a maximized delivery of fluid to an assay layer 90, other arrays of such patterns about their trunks 35/45/55 may accomplish substantially the same tasks.

In certain embodiments, a separation β between the stump 6 of a stalk 2 and the elbow 5 of an adjacent stalk 2 maximizes the dissemination of sample fluid, avoids trapped air and creation of vortices, and reduces competition by sample flows from different branches to fill the continuous region. In other words, separation β between the stump 6 of a stalk 2 and the elbow 5 of an adjacent stalk 2 may provide a benefit to optimized dissemination of fluid samples in device 100.

In certain embodiments, each layer of device 100 may be designed with a pattern of holes matching the positions of a plurality of pegs on an aligner as well as for replicates of additional cut or plotted patterns. In certain embodiments, all layers 20-80 may be cut using a laser cutter except the paper layer 90, which may require a custom-designed hybrid cutter-plotter. e.g., the hydrophilic polycarbonate 20/30/40/50/60/70/80 layers, DSA 112, and lamination layer 95 were laser cut. In certain embodiments, the polycarbonate and DSA layers may be received with protective layers on both sides, which were left in place during cutting and removed immediately before assembly. In certain embodiments, a hybrid cutter-plotter may comprise an X-, Y-motor with both a pen plotter to pattern the hydrophobic barriers 92 and a laser for cutting the assay zones 90.

Referring now to the illustrative embodiment depicted in FIGS. 6A and 6B, a device 100 may be aligned with a color standard palette 200 having one or more colors matching the colors of assay spots 91 on assay layer 90 of device 100. Each of device 100 and palette 200 may be situated within a photographic analysis container ("PAC") 300 so that they are disposed on a floor 301 of the PAC and surrounded by three walls 306 extending upwardly from floor 301 and terminating in a ceiling 302 having an aperture 304 spanning from ceiling 302 to roof 305. In certain embodiments, the analysis using photographic technologies, such as those found on a smart phone or other photographic device 400 may be maximized by use of a door 308 having retention means 309 for holding door 308 to PAC 300 leaving only photographic device 400 visible atop roof 305.

In certain embodiments, a photographic device 400 may be a smart phone. Referring to FIGS. 6A and 6B, a smart phone 400 may have a complementary metal-oxide-semiconductor sensor (CMOS) which may store the image of the colorimetric assays 91 in non-linearized sRGB (red, green, blue) values. In certain embodiments where a smartphone camera may be used as a photodetector, PAC 300 may be provided to stabilize the smartphone camera and compensate for the ambient light present in the environment.

In certain embodiments, a PAC 300 may have dimensions of 15×9.5×16.5 cm, providing enough distance from the microfluidic device 100 to uniformly distribute the single flash light over the entire device. A mobile device 400, such as a smartphone or any other suitable device with a digital camera and a processing unit, may be placed on the roof 305 of PAC 300, overlapping the aperture 304 for the placement of an exemplar mobile device 400 camera lens and flash, while the microfluidic device 100 may be placed inside the PAC 300 directly underneath the camera lens. In certain embodiments, a color reference chart 200, which may contain 15 color regions, may be placed adjacent to the microfluidic device 100 to provide for color correction in color mean intensities captured in the image of mobile device 400 (similar to color-rendition charts utilized in photography).

In an alternative method, device 100 and palette 200 can be imaged outside of photographic analysis container using a photographic device 400. The image can then be processed by a machine learning algorithms to filter the ambient lighting and/or color noise and quantify the result of the testing performed by each assay.

In one example, a simple RGB analysis of test assays may not produce distinguishable concentration levels of the sample. Therefore, after linearization of the raw data, the RGB intensity-values may be converted to xyY values and plotted pursuant to an appropriate colorimetric standard, such as, for example, color space set by the International Commission on Illumination established in 1931 ("CIE 1931"). In certain embodiments, linearization of sRGB values may be achieved through the following equations:

$$R_{linear} = \left(\frac{0.055. + R_{srgb}}{1.055}\right)^{2.4}$$

$$G_{linear} = \left(\frac{0.055. + G_{srgb}}{1.055}\right)^{2.4}$$

$$B_{linear} = \left(\frac{0.055. + B_{srgb}}{1.055}\right)^{2.4}$$

Linearized RGB values, once obtained from the above equations, may be converted to corresponding CIE 1931 XYZ color space and then to CIE 1931 xyY color space if those values lie between 0 and 255 on the color scale. The following equations may be used for such conversions from the linearized RGB values:

$$\begin{bmatrix} X \\ Y \\ Z \end{bmatrix} = \begin{bmatrix} 0.4124 & 0.3576 & 0.1805 \\ 0.2126 & 0.7152 & 0.0722 \\ 0.0193 & 0.1192 & 0.9505 \end{bmatrix} \begin{bmatrix} R_{linear} \\ G_{linear} \\ B_{linear} \end{bmatrix}$$

Following the above equation according to certain embodiments, X, Y, Z tristimulus values may then be converted to xy chromaticity values, where the Y parameter represents luminance of the color, using the following equations:

$$x = X/(X+Y+Z)$$

$$y = Y/(X+Y+Z)$$

Wherein, the xyY parameters define the 2D chromaticity diagram in the CIE 1931 color space. By creating a calibration curve from the standard analyte solutions, the chromaticity diagram may be used to predict the outcome of color mixtures, aiding in the identification and quantification of complicated colorimetric assays.

In certain embodiments, use of an application on a mobile device 400 may provide access to infographics, which may include use of images taken by the device, sent to a backend web service, and thereafter receiving and visualizing the result of the test.

Accordingly, in a sample analysis method using the device 100 described, an application stored on the mobile device 400 may receive details of the sample volume from the user and then prompts positioning the mobile device 400 over the aperture 304 on PAC 300 for imaging color changes in detection zones 91. In accordance with at least one aspect of this analysis method, the flash of the mobile device 400, when embodied as a smart phone, is on, in order to achieve a more accurate luminance. In further accordance with this methodology, a mobile device application may send the image to a cloud web service developed in C # and hosted on Microsoft Azure for quantification of fluid sample parameters. In certain embodiments, the cloud web service may quantify parameters particular to semen and fertility analysis. In these aforementioned embodiments, a backend web service may locate the color circles in both the device and standard color palette and calculate the average color within them.

In certain embodiments of a parameter quantization using the cloud web service and the device 100, a polynomial regression may be performed for the color correction of detection zones 91 using a standard color pallet 200. Further correction may also occur by adjusting the brightness values by using the white values measured outside of each circle. The final color values may then be converted to appropriate parameters, such as, for example, semen parameters, using calibration equations, which may then be sent back to the app in a restful format where it may be displayed for the user through several visualizations of the application on device 400. These values, along with debugging information from the analysis process, may be stored along with the image within available online platform storage systems, e.g., the "blob storage" offered by Microsoft Azure (Microsoft Corporation, Redmond, WA).

In certain embodiments where the assay layer 90 may be used for detection of fertility parameters of a semen sample, for example, a sperm count assay, sperm motility, pH assay, and fructose assay, particular colorimetric detection schemes may be implemented to properly define these various parameters.

In accordance with sperm count assay determination in certain embodiments, a sperm count assay may represent a measure of colorimetric change of yellow tetrazolium dye to purple formazan by the diaphorase flavoprotein enzyme present in metabolically active human sperm to quantify sperm count. In certain embodiments, use of device 100 may allow for classification of a sperm count to be low (less than 15 M/ml), moderate (between 15 and 55 M/ml), and high (above 55 M/ml). In certain embodiments, a characteristic curve for sperm count concentration may be $C = -867x - 1762y + 1440x^2 + 1887y^2 + 524$, having an R-squared value of 0.97.

In accordance with pH sensitivity determination in certain embodiments, an analysis involves multiplexing three pH indicators, 0.8 mg/mL bromocresol green, 0.8 mg/mL bromothymol blue, and 0.4 mg/mL thymol blue. The calibration curve equations and the corresponding correlation coefficient (R-squared) values obtained for the three indicators may include the following (where z is pH concentration, x and y are color values of CIE 1931 xyY color space):

For Bromocresol green, $z=143.3x-354y-242.3x^2+510.6y^2+45.1$

For Bromothymol blue, $z=249.3x-173.4y-385.1x^2+223.8y^2+0.716$

For Thymol blue, $z=545.1x-62.4y-847.4x^2+95.54y^2-67.5$

In certain embodiments, given any combination of three colors, the aforementioned calibration curves may be used to estimate the colors. However, in certain embodiments, only one of the curves may be selected to determine the exact pH value.

In certain embodiments, a curve for bromocresol green may be used to identify the pH in the range of 4 to 6, a curve for bromothymol blue may be used to identify pH in the range of 6 to 9, and a curve for thymol Blue may be used to identify pH in the range of 8 to 10.

In accordance with fructose determination in certain embodiments, a fructose assay may be based on a glucose assay known to those skilled in the art, such as the Glucose (GO) Assay Kit by Sigma Aldrich of St. Louis, Mo. with the addition of an enzyme that converts the fructose in the semen to glucose, which may be measured by the assay reagents, such as phosphoglucose isomerase by Sigma Aldrich of St. Louis, Missouri.

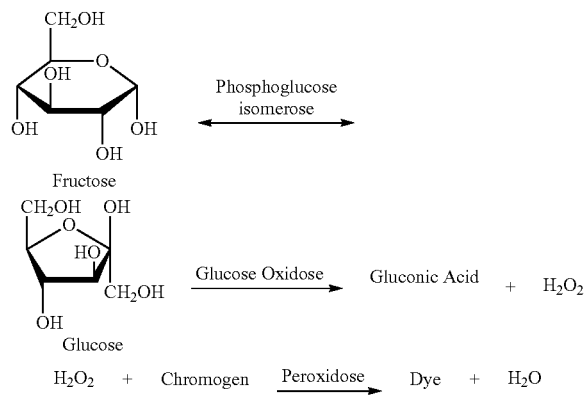

In accordance with sperm motility determination in certain embodiments, a motility assay may be based on a cell metabolic activity assay known to those skilled in the art, such as the resazurin metabolism assay Kit by Sigma Aldrich of St. Louis, Missouri. Any other sperm motility assay is contemplated herein.

In accordance with at least one aspect of this disclosure, a fluid analysis device can be configured to receive a test fluid and to uniformly distribute the test fluid to a plurality of fluidly isolated assays. In certain embodiments, the test fluid can be semen.

In accordance with at least one aspect of this disclosure, a method can include analyzing a device as disclosed herein, e.g., as described above, in photographic analysis container using an imaging device and an image processor (e.g, a smartphone, tablet, etc.). The method can include any other suitable method and/or portions thereof.

It is contemplated that one or more methods of analysis can be embodied as one or more modules having any suitable hardware and/or software configured to analyze the assays (e.g., a smartphone app configured to gather and/or analyze a smartphone photo of the assays). Accordingly, as will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in certain, to A only (optionally including elements other than B); in certain embodiments, to B only (optionally including elements other than A); in certain embodiments, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A fluid analysis device, comprising:
a fluid inlet opening configured to receive a test fluid;
one or more distribution layers comprising one or more fluid distribution channels;
one or more assay layers comprising a plurality of assays fluidly isolated from each other and configured to receive the test fluid from the one or more fluid distribution channels, wherein each of the plurality of assays is configured to generate an assay result within the fluid analysis device; and
one or more vertical channel layers disposed between the one or more distribution layers and the one or more assays layers and having a plurality of fluidly isolated vertical channels, the plurality of vertical channels being configured to align a portion of the one or more fluid distribution channels with a respective assay on the assay layer, and
wherein the one or more distribution channels: (a) are in fluid communication with the fluid inlet opening and configured to receive and distribute the test fluid from the fluid inlet opening using a passive self-loading mechanism; (b) are made entirely from a polymer; and (c) comprise a plurality of fluid paths that (i) extend from a trunk portion, and (ii) reduce in flow area to cause substantially even distribution to each terminus and further wherein each fluid path (1) terminates into one or more terminus in fluid communication with the one or more vertical channels, wherein only the one or more terminus are in fluid communication with the vertical channels; (2) includes a branch in fluid communication with the trunk and having a branch flow area, a stalk in fluid communication with the branch, the stalk having a diameter smaller than the branch and a stalk flow area smaller than the branch flow area, and one or more stems in fluid communication with the stalk, the stem having a diameter smaller than the stalk and a stem flow area smaller than the stalk flow area; and (3) is fluidly isolated from the other fluid paths to prevent bubble trapping, and further wherein the fluid analysis device uniformly distributes the test fluid to the plurality of assays.

2. The device of claim 1, further comprising an inlet layer defining the fluid inlet opening.

3. The device of claim 2, wherein the one or more distribution layers are attached to the inlet layer and forming the one or more fluid distribution channels.

4. The device of claim 2, wherein the inlet layer includes a plurality of vent holes defined therein in fluid communication with the one or more fluid distribution channels to allow air flow through the plurality of vent holes.

5. The device of claim 1, wherein the one or more distribution layers include and/or are formed from a channel layer material that is configured to be wetted by the test fluid.

6. The device of claim 5, wherein the channel layer material is hydrophilic.

7. The device of claim 1, wherein the one or more assay layers is made of an assay layer material that is configured to be wetted by the test fluid, wherein each assay is surrounded by a non-wettable material to fluidly isolate each assay from each other and/or from the assay layer material.

8. The device of claim 7, further comprising a clear bottom layer disposed on an underside of the assay layer and configured to allow viewing of each assay result and/or each assay.

9. The device of claim 1, further comprising a mask connected to the one or more vertical channel layers and configured to permanently or selectively reduce and/or filter a flow area of the one or more vertical channels.

10. The device of claim 1, further comprising one or more adhesive layers configured to adhere one or more other layers together, the one or more adhesive layers comprising one or more complimentary channels and/or holes defined therein to allow flow therethrough.

11. The device of claim 1, further comprising an inlet reservoir in fluid communication with the inlet opening and configured to receive the test fluid from a user.

12. The device of claim 1, wherein the test fluid is semen.

13. The device of claim 1, wherein the plurality of assays comprise one or more assay reagents for generating the assay result.

* * * * *